(12) United States Patent
Nieuwenhuis et al.

(10) Patent No.: US 7,295,310 B2
(45) Date of Patent: Nov. 13, 2007

(54) APPARATUS FOR DETERMINING THE SHAPE AND/OR SIZE OF LITTLE PARTICLES

(75) Inventors: Jeroen Hans Nieuwenhuis, Delft (NL); Gerrit Wijnand Lubking, deceased, late of Utrecht (NL); by Gerrit Yki Warries, legal represenitive, Utrecht (NL); Michael Johannes Vellekoop, Vienna (NL)

(73) Assignee: Technische Universiteit Delft, Delft (NL)

( * ) Notice: Subject to any disclaimer, the term of this patent is extended or adjusted under 35 U.S.C. 154(b) by 122 days.

(21) Appl. No.: 11/075,683

(22) Filed: Mar. 9, 2005

(65) Prior Publication Data

US 2005/0248761 A1 Nov. 10, 2005

Related U.S. Application Data

(63) Continuation-in-part of application No. 10/336,143, filed on Jan. 3, 2003, now abandoned, which is a continuation of application No. PCT/NL01/00518, filed on Jul. 6, 2001.

(30) Foreign Application Priority Data

Jul. 6, 2000 (NL) .................................. 1015640

(51) Int. Cl.
*G01N 15/02* (2006.01)

(52) U.S. Cl. ...................................................... 356/335
(58) Field of Classification Search ..................... None
See application file for complete search history.

(56) References Cited

U.S. PATENT DOCUMENTS

| 5,101,978 | A | 4/1992 | Marcus |
| 5,255,069 | A | 10/1993 | Duarte |
| 5,513,004 | A | 4/1996 | Naqwi et al. |
| 5,572,320 | A | 11/1996 | Reintjes et al. |
| 5,825,477 | A | 10/1998 | Furuie |
| 5,933,233 | A | 8/1999 | Gunther |
| 6,101,978 | A | 8/2000 | Steckel |
| 6,118,531 | A | 9/2000 | Hertel et al. |

FOREIGN PATENT DOCUMENTS

| DE | 196 28 348 C1 | 9/1997 |
| GB | 2 326 229 A | 12/1998 |

*Primary Examiner*—Michael P. Stafira
(74) *Attorney, Agent, or Firm*—Jeffrey D. Myers; Janeen Vilven; Samantha A. Updegraff

(57) ABSTRACT

The invention relates to an apparatus for determining the shape and/or size of small particles, comprising a cell into which the particles are placed, at least one light source for illuminating the particles, and at least one one-dimensional image sensor for measuring an image of the illuminated particles. The cell is embodied as a conduit through which the particles can be transported, and the image sensor is placed in the immediate vicinity of the conduit or into the conduit.

7 Claims, 4 Drawing Sheets

APPARATUS FOR DETERMINING THE SHAPE AND/OR SIZE OF LITTLE PARTICLES

CROSS-REFERENCE TO REALATED APPLICATIONS

This application is a continuation in part of U.S. patent application Ser. No. 10/336,143 filed Jan. 3, 2003, now abandoned entitled Apparatus For Determining The Shape And/Or Size Of Little Particles, which in turn is a continuation of international Patent Application PCT/NL01/00518 (WO02/03049A1), filed on Jul. 6, 2001, which claims priority to Netherlands Patent Application NL 1015640, filed on Jul. 6, 2000, and the specification of each of the foregoing is incorporated herein by reference.

STATEMENT REGARDING FEDERALLY SPONSORED RESEARCH OR DEVELOPMENT (Not Applicable)

INCORPORATION BY REFERENCE OF MATERIAL SUBMITTED ON A COMPACT DISC (Not Applicable)

COPYRIGHTED MATERIAL (Not Applicable)

BACKGROUND OF THE INVENTION

1. Field of the Invention (Technical Field)

The invention relates to an apparatus for determining the shape and/or size of small particles, comprising a cell into which the particles are placed, at least one light source for illuminating the particles, and at least one one-dimensional image sensor for measuring an image of the illuminated particles. Within the frame of the present invention, small particles are understood to be particles having a size of up to about 200 µm in diameter.

2. Description of Related Art

From the prior art, various instruments are known with which the size or shape of particles can be determined. However, the problem with these known devices is that they are complex and expensive, and that the shape of the particles is determined in a very indirect manner and therefore does not provide any direct information with regard to shape.

From U.S. Pat. No. 5,764,358 a method and apparatus is known for the determination of the shape characteristics of particles, which particles are fed through a transparent cell through which a light beam is projected. The intensity of the light scattered by the particles is measured with a detector comprising one or more concentric rings or parts of rings, at least one of which is provided with one or more isolated segments. The rings and the isolated segments are coupled to an energy meter for the determination of amplitude classes. The shape characteristics of the particles are determined on the basis of the thus provided amplitude classes.

U.S. Pat. No. 4,070,113 relates to a system for classifying the various types of blood cells by using a laser beam. The light scattered by the blood cells is applied to a detector array, which provides a voltage spectrum that is representative of the spatial relationship of the cells. This voltage spectrum is compared with known spectra that are representative of different blood cell classes. When a good fit is found, the blood cell is assigned to the respective blood cell class.

U.S. Pat. No. 4,173,415 relates to a method and apparatus for rapidly characterizing and differentiating large organic cells. To this end, individual cells are illuminated with monochromatic light, which produces a light-scattering pattern that is measured with the aid of an array of detectors. The resulting measurement is used for the identification and characterization of the cell.

Characteristic of the above-discussed prior art is that use is made of the scattering of the light with which the particles to be analyzed are illuminated. The image obtained at the detector array is per definition an imprecise image so that the determination of the particle shape, though not impossible, is laborious and exhibits considerable inaccuracies.

U.S. Pat. No. 5,548,395 relates to an apparatus for analyzing particles, wherein a one-dimensional image sensor is used which extends transversely to the flow direction of the particles, and which serves to catch images of the shadows of the particles that are illuminated by a light beam, for example, a laser beam.

From U.S. Pat. No. 5,572,320 an apparatus for the classification of particles is known, wherein the particles are fed through a conduit and wherein a light source that is oriented transversely to the conduit, illuminates the particles. With the aid of an optical system the resulting shadows from the particles are detected by an image sensor provided behind the optical system. The optical system serves to enlarge the shadows to allow a desirable resolution to be realized. The conduit applied in U.S. Pat. No. 5,572,320 is sufficiently thin that the diffraction pattern of light exiting it is characteristic of the optical near field. Correspondingly, the preamble of claim 1 reads on U.S. Pat. No. 5,572,320.

U.S. Pat. No. 5,825,477 relates to an apparatus for measuring a particle's morphology in solution, wherein a light emitting source illuminates a particle whose image is captured by an image capturing device having a shutter and optics such as a video camera. U.S. Pat. No. 5,825,477 is silent as to positioning of the image capture device such that the image capture device is in the so-called near field (Fresnel zone) of the particle to be imaged.

One aspect of the present invention provides an apparatus to obtain information about the shape and size of individual particles quickly and simply, that is to say without the need of numerous complicated calculations on the basis of the measured images. Another object of the present invention provides a relatively simple apparatus.

BRIEF DESCRIPTION OF THE SEVERAL VIEWS OF THE DRAWINGS

The accompanying drawings, which are incorporated into and form part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

An apparatus according to several embodiments of the present invention is characterized in that the same is provided with multiple light sources and image sensors that are grouped around the conduit to enable them to form an image. According to another embodiment of the present invention, multiple light sensors and image sensors are positioned about an aperture formed through a (silicon) slice of, for example, 0.5 mm thickness, wherein a two-dimensional shot is taken (tomography) by means of light sources and photodiodes around the rim of the aperture.

The moment a particle flows through the light beam, a cast shadow will fall on one or several light-sensitive elements of the image sensor. The light sensitive elements operate without the need of a shutter or optics. Preferably the light-sensitive elements are read out repeatedly, and the shape and/or size of the particles is derived from a combination of the thus repeatedly carried out measurement. The result, after applying a few simple computations is—as it were—a photo-record of the particle.

One aspect of the present invention is that the light-sensitive elements are located in the so-called near field (Fresnel zone) of the particles, so that a direct optical record is obtained of the particles, while substantially avoiding the influence of scattering light. An important advantage provided by the invention in comparison with the prior art is that it makes it possible to determine the size and shape of each individual particle. The apparatus to be used for this purpose can be realized inexpensively and its operation is simple. An optical system for the registration of the particles is not necessary.

In order to ensure that the image sensor is located in the near field the conduit used may, for example, be a conduit that is so small that the particles are bound to be in the right position. However, within the frame of the invention it is also conceivable to use a conduit in which hydrodynamic focusing occurs with which the stream of particles may be positioned on a previously determined location in the conduit. It is also conceivable to apply a different external force for the positioning of the particles.

Figure 1:
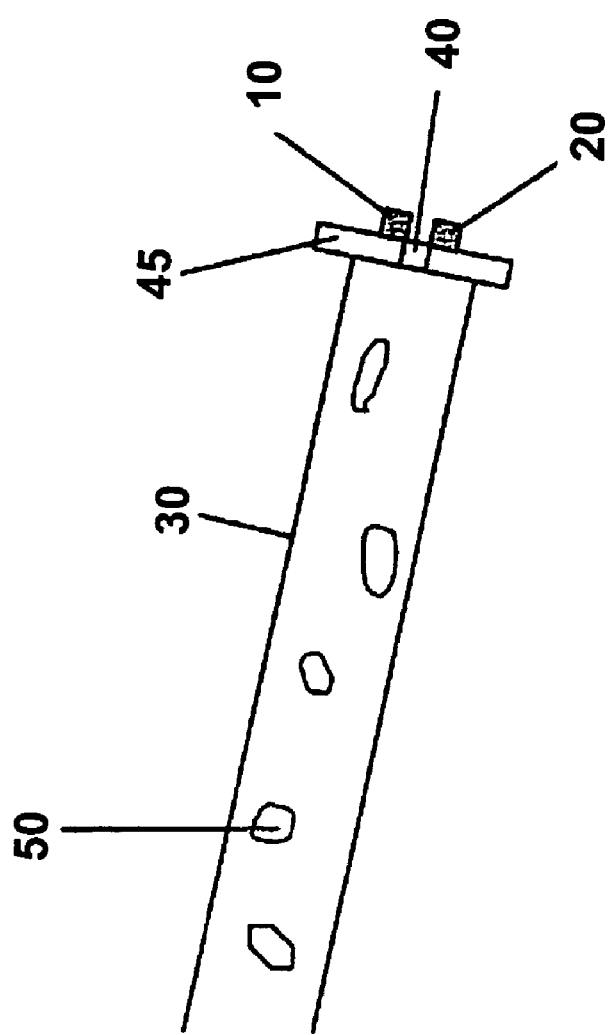
FIG. 1 is an illustration showing a side view of a preferred embodiment of the present invention.

Referring now to FIG.-1, an apparatus according to one embodiment of the present invention is illustrated wherein multiple light sources 10 and image sensors 20 are grouped around the conduit 30 to enable them to form an image.

Figure 2:
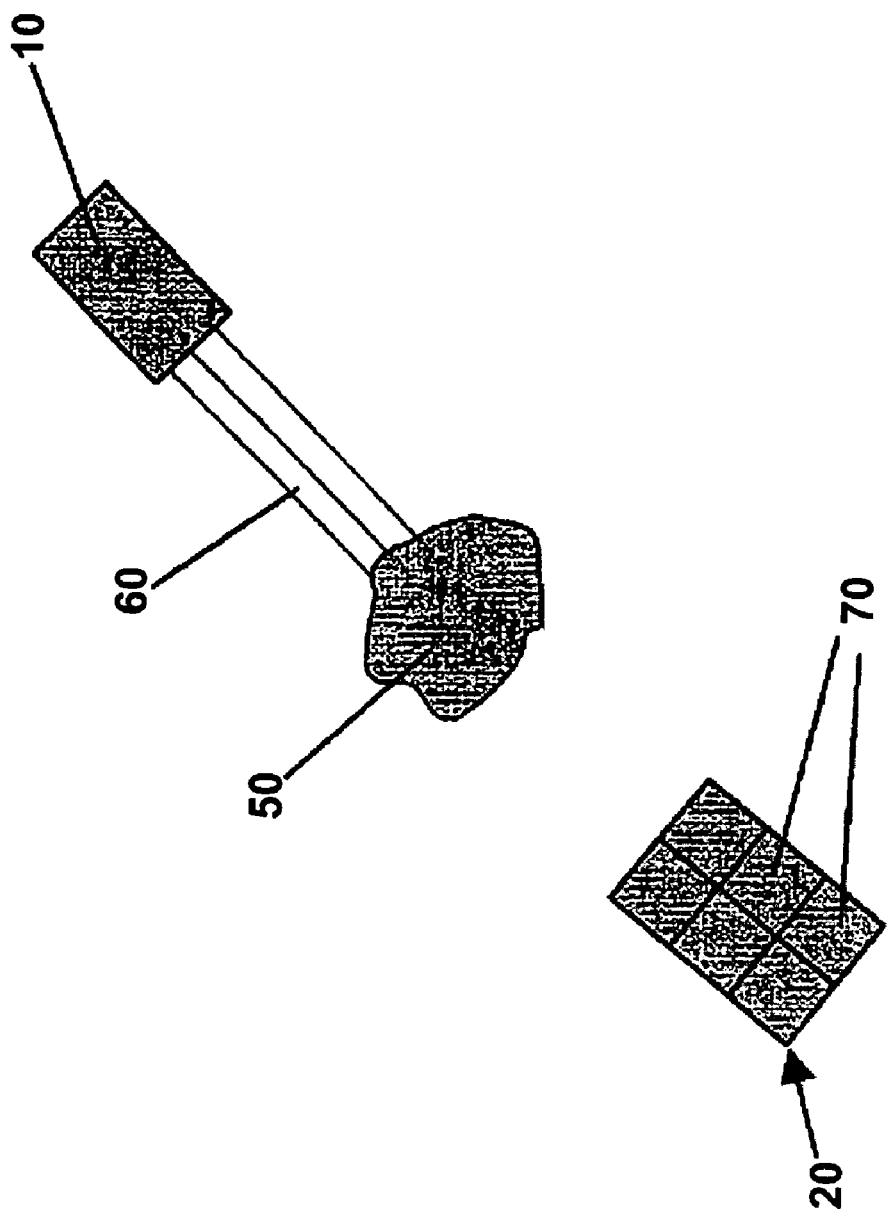
FIG. 2 is an illustration of a particle passing between the light source and an image sensor according to one embodiment of the present invention.

FIG.-2 illustrates the passage of a particle at the moment a particle 50 flows through the light beam 60, to cast a shadow upon one or several light-sensitive elements 70 of the image sensor. Preferably the light-sensitive elements are read out repeatedly, and the shape and/or size of the particles is derived from a combination of the thus repeatedly carried out measurement. The result, after applying a few simple computations is a photo-record of the particle. An aspect of the invention is that the light-sensitive elements 70 are located in the so-called near field (Fresnel zone) of the particles 50, so that a direct optical record is obtained of the particles, while substantially avoiding the influence of scattering light. An important advantage provided by the invention in comparison with the prior art is that it makes it possible to determine the size and shape of each individual particle. The apparatus to be used for this purpose can be realized inexpensively and its operation is simple. An optical system such as a camera for the registration of the particles is not necessary.

Figure 3:
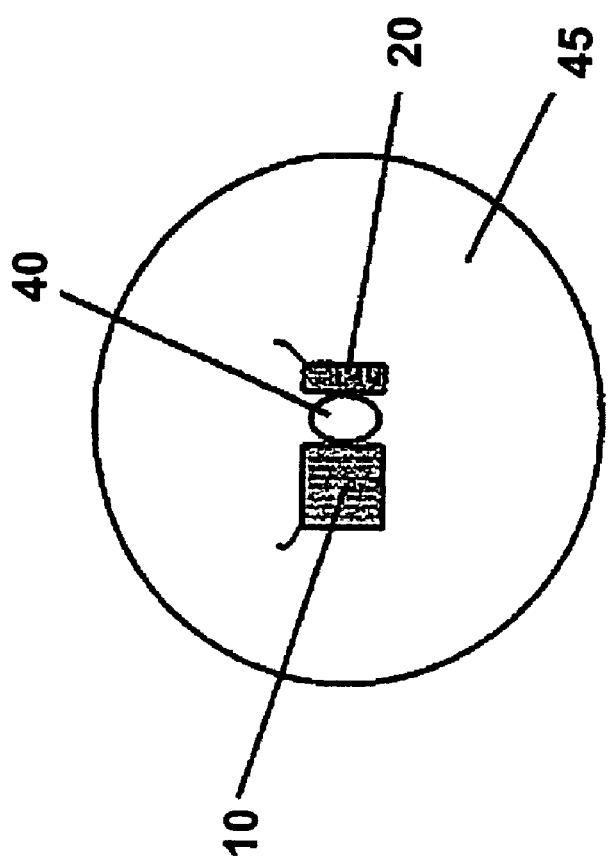
FIG. 3 is an illustration of an end view of a preferred embodiment of the present invention.

Referring now to FIG.-3, an apparatus of having a small aperture 40 straight through a (silicon) slice of 45, for example, 0.5 mm thickness, wherein a two-dimensional shot is taken (tomography) by means of light sources 10 and photodiodes 20 around the rim of the aperture 40.

Figure 4:
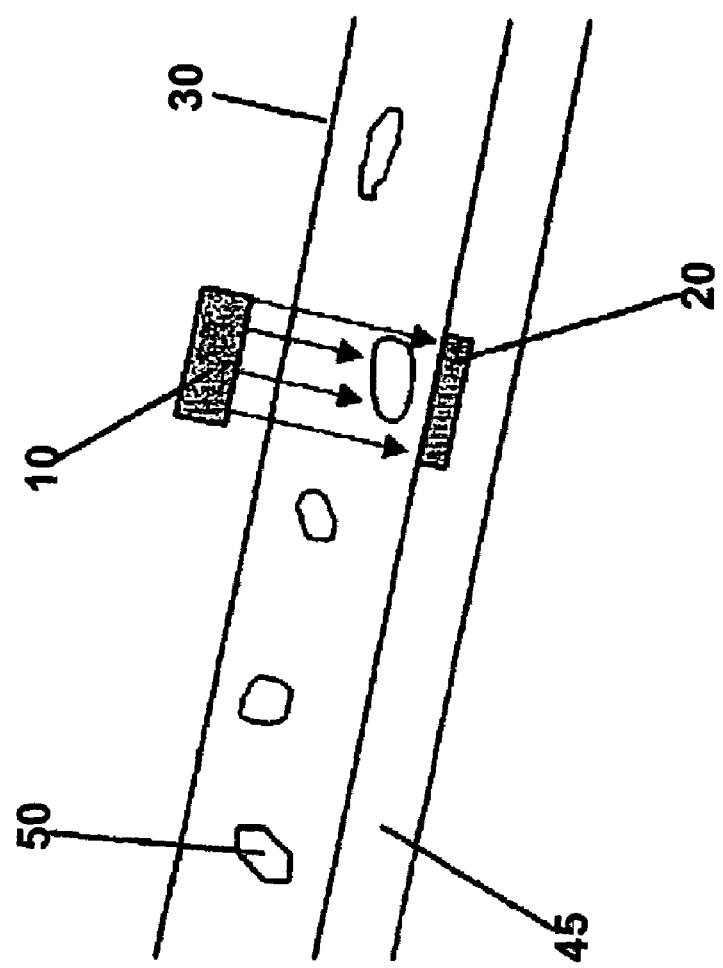
FIG. 4 is an illustration of a particle passing between a light source and an image sensor according to one embodiment of the present invention.

Referring now to FIG.-4, an apparatus according to one embodiment of the present invention is illustrated wherein one or more light sources 10 produce a light beam that is detected by one or more image sensors 20. A particle 50 passes between light source 10 and image sensors 20 such that a direct optical record is obtained of a particle. Light source 10 is positioned about the conduit to be opposite the image sensors 20. A silica chip 45 having integrated therein an image sensor 20 borders the conduit 30. Both the light source and image sensor are integrated into the conduit wall.

In order to ensure that the image sensor 20 is located in the near field, the conduit 30 used may, for example, be a conduit that is so small that the particles 50 are bound to be in the right position. However, within the frame of the invention it is also conceivable to use a conduit in which hydrodynamic focusing occurs with which the stream of particles may be positioned on a previously determined location in the conduit 30. It is also conceivable to apply a different external force for the positioning of the particles.

The conduit 30 may be made of, for example, silicon or glass. The light source 10 then provides light that is directed transversely to the conduit 30, in the direction of the image sensor 20. There is no need to use an optical system for the registration of the particles 50.

For the one-dimensional image sensor there are various possible implementations. For example, an array of photodiodes, CCD elements, phototransistors, and the like may be used. A suitable embodiment of the apparatus is characterized in that the image sensor comprises a structure of elongated photosensitive elements that are placed in the conduit and substantially at right angles to the flow of particles through the conduit.

An alternative embodiment is characterized in that the image sensor comprises a one-dimensional array of light-sensitive elements that are placed into the conduit, and substantially at right angles to the flow of particles through the conduit. Advantageously the image sensor is embodied such that it comprises two one-dimensional arrays of light-sensitive elements placed one behind the other in the conduit, and substantially at right angles to the flow of the particles through the conduit. This endows the image sensor with a greater robustness, while in addition providing a higher resolution. In this manner it is also possible to determine the speed of the particles.

This may be achieved in particular if the image sensor is embodied such that, viewed in the flow direction, the light-sensitive elements of the first array are placed next to the light-sensitive elements of the second array.

In another aspect of the invention, the apparatus is characterized in that the same comprises a plurality of conduits arranged next to each other, each of them provided with at least one image sensor.

The fact that the apparatus according to the invention is especially suitable to be embodied in an integrated circuit, makes it possible in this manner to provide an apparatus that is capable of quickly analyzing large quantities of particles by processing them parallel with the thus embodied apparatus. This is especially useful with medical applications, where it is necessary for large numbers of cells to be analyzed in a short time.

In a further proposed embodiment variant, the apparatus may advantageously be embodied such that the same comprises a selection actuator for directing particles through one of the conduits. This provides a system of so-called sample enrichment, in which large quantities of particles can be analyzed automatically, and particles deviating from a predetermined standard can be selected to be separately further analyzed in more detail.

It is believed that the afore-given description of the invention is sufficiently clear and complete for a person skilled in the art, so that further elucidation based on an Example or the like may be omitted. It is further remarked, that the above description contains an elucidation with regard to the appended claims, without in any way limiting the protective scope derived from these claims.

What is claimed is:

1. An apparatus for determining the shape and/or size of small particles, comprising a conduit through which the particles can be transported, at least one light source for illuminating the particles, and at least one one-dimensional image sensor or sensors for measuring an image of the illuminated particles, said image sensor or sensors being placed in the immediate vicinity of the conduit, or into the conduit, in the near field (Fresnel zone) of the particles, wherein the image sensor or sensors receive light being characteristic for the optical field without use of intermediate imaging optics, and wherein the image sensor comprises a structure of elongated photosensitive elements that are placed in the conduit and substantially at right angles to the flow of particles through the conduit.

2. An apparatus according to claim 1 wherein the image sensor comprises at least one one-dimensional array of light-sensitive elements that are placed into the conduit, and substantially at right angles to the flow of particles through the conduit.

3. An apparatus according to claim 1 wherein the image sensor comprises two one-dimensional arrays of light-sensitive elements placed one behind the other in the conduit, and substantially at right angles to the flow of the particles through the conduit.

4. An apparatus according to claim 3, wherein viewed in the flow direction, the light-sensitive elements of the first array are placed next to the light-sensitive elements of the second array.

5. An apparatus according to claim 1 wherein the apparatus comprises a plurality of conduits arranged next to each other, each of them provided with at least one image sensor.

6. An apparatus according to claim 5, wherein the apparatus comprises a selection actuator for directing particles through one of the conduits.

7. An apparatus according to claim 1 wherein the apparatus is provided with multiple light sources and image sensors that are grouped around the conduit for the formation of the image.

* * * * *